(12) United States Patent
Lambers

(10) Patent No.: US 7,597,899 B2
(45) Date of Patent: Oct. 6, 2009

(54) COMPOSITIONS COMPRISING A COMBINATION OF A FREE SPHINGOID BASE AND CERAMIDE AND USES THEREOF

(75) Inventor: Johannes Wilhelmus Jacobus Lambers, Pijnacker (NL)

(73) Assignee: Cosmoferm B.V., Delft (NL)

( * ) Notice: Subject to any disclaimer, the term of this patent is extended or adjusted under 35 U.S.C. 154(b) by 347 days.

(21) Appl. No.: 10/463,277

(22) Filed: Jun. 17, 2003

(65) Prior Publication Data

US 2003/0215414 A1  Nov. 20, 2003

Related U.S. Application Data

(63) Continuation of application No. 09/367,033, filed as application No. PCT/EP98/08121 on Dec. 7, 1998, now abandoned.

(30) Foreign Application Priority Data

Dec. 5, 1997  (EP)  ................................. 97203824

(51) Int. Cl.
*A61K 8/02* (2006.01)
*C11C 3/00* (2006.01)
(52) U.S. Cl. ........................................ 424/401; 554/66
(58) Field of Classification Search ................. 424/401; 514/859, 887; 554/66
See application file for complete search history.

(56) References Cited

U.S. PATENT DOCUMENTS

| | | | |
|---|---|---|---|
| 5,565,207 A | 10/1996 | Kashibuchi | |
| 5,578,641 A | 11/1996 | Jackson et al. | |
| 5,627,056 A | * 5/1997 | Casey et al. | ................. 435/134 |
| 5,693,677 A | 12/1997 | Lambers et al. | |
| 5,869,711 A | 2/1999 | McAtee | |
| 5,939,077 A | 8/1999 | Saint-Leger | |

FOREIGN PATENT DOCUMENTS

| | | |
|---|---|---|
| JP | 61-26000 | 11/1986 |
| WO | WO 93/20038 | 10/1993 |
| WO | WO 94/00127 | 1/1994 |
| WO | WO 95/11881 | 5/1995 |
| WO | WO 95/25716 | 9/1995 |
| WO | WO 95/29151 | 11/1995 |
| WO | WO 96/10557 | 4/1996 |
| WO | WO 97/09307 | * 3/1997 |

OTHER PUBLICATIONS

Bouwstra, J.A. et al.,"*Phase Behavior Of Isolated Skin Lipids*," J. LIPID RES., (1996) 37:999-1011.

* cited by examiner

*Primary Examiner*—Sreeni Padmanabhan
*Assistant Examiner*—Renee Claytor
(74) *Attorney, Agent, or Firm*—Frommer Lawrence & Haug LLP

(57) ABSTRACT

The present invention discloses a composition for topical use comprising a free sphingoid base and a ceramide. The compositions of the invention are suitable for application to skin conditions associated with an impaired barrier function, in particular to skin conditions further associated with a deranged regulation of cell growth and differentiation, an inflammatory condition and/or an infectious state.

15 Claims, No Drawings

COMPOSITIONS COMPRISING A COMBINATION OF A FREE SPHINGOID BASE AND CERAMIDE AND USES THEREOF

This application is a continuation of application U.S. Ser. No. 09/367,033, filed Sep. 13, 1999 now abandoned, still pending and herein incorporated by reference, which in turn was filed pursuant to 35 USC §371 from international application number PCT/EP98/08121, filed Dec. 7, 1998 and also incorporated herein by reference, which in turn claims priority to EP application 97203824, filed Dec. 5, 1997.

FIELD OF THE INVENTION

The present invention relates to the field of topical use of compositions comprising a selected combination of sphingolipids.

BACKGROUND OF THE INVENTION

The human skin forms a structural and adapted barrier to the environment. It further plays an important physiological role since it provides not only protection and thermoregulation, but also has a metabolic and sensorial function and storage capacity.

It has been shown that the lipid composition of the epidermal cells within the skin changes considerably when the cells migrate to the outer surface and differentiate. The cells in the basal layer contain a complex lipid composition, with phospholipids as the major constituent In the granular layer the phospholipid content is diminished while the amount of cerebrosides (glycosylceramides), ceramides, cholesterol and cholesterol sulphate is increased as result of de novo synthesis and storage into the so-called lamellar bodies. In the outermost lipid layer of the epidermis, called the stratum corneum (horny layer) the phospholipids and cerebrosides have vanished completely. The most abundant lipids in this layer are ceramides, which mainly have been formed by enzymatic deglycosylation of cerebrosides.

The barrier function of the skin mainly is provided by the stratum corneum. The stratum corneum consists of corneocytes embedded in an extracellular matrix of multiple bilayers of lipids. The intercellular lipid phase of the stratum corneum has roughly the following composition: 40% ceramides, 25% cholesterol, 10% cholesteryl sulphate and 25% free fatty acids. As long as the "bricks and mortar". construction of the stratum corneum is not affected, the skin is provided with both a perfect protective layer and a filter-active permeability layer.

Several categories of skin conditions or disorders are known which are characterized by an impaired lipid barrier function, further accompanied by characteristics like a deranged regulation of cell growth and differentiation (e.g. hyperproliferation and/or decreased differentiation of keratinocytes, decreased desquamation of corneocytes), an inflammatory response and/or an infectious state. In these skin conditions, the skin generally displays a rough, red, dry, chapped and/or swollen character. Typical examples of such disorders are xerosis, acne vulgaris, psoriasis, atopic dermatitis, contact dermatitis, UV-induced erythema, and the like.

Satisfactory treatment methods for these disorders presently are not available. Emollient creams and lotions may relieve part of the symptoms, but often only temporarily. Conventional anti-inflammatory creams, of which corticosteroid creams form the main part, are more effective for the treatment of certain disorders but continued use may reduce the effectiveness of the treatment and/or may give side reactions. In addition, conventional antiinflammatory as well as antimicrobial creams typically are not adapted to restore an impaired barrier function.

Ceramides are generally applied in cosmetics because of their moisture-retaining properties (see for instance Japanese patent application J61-260008).

In International patent application WO94/00127 it has been described that formulations containing specific lipid mixtures should be applied for an optimal treatment of skin disorders associated with a disrupted epidermal barrier. Said lipid mixtures comprise lipids selected from the three major classes of naturally-occurring epidermal lipids, i.e. the classes of ceramides, cholesterol and free fatty acids. However, in order to be optimally effective for skin conditions associated with inflammatory or infectious phenomena, these formulations have to be applied together with conventionally used therapeutic agents Surprisingly, it is shown by the present invention that topical compositions comprising a combination of a free sphingoid base and a ceramide have a beneficial effect when applied on skin conditions associated with an impaired barrier function, and especially when applied on skin conditions further associated with a deranged regulation of cell growth and differentiation, inflammatory and/or infectious phenomena.

DESCRIPTION OF THE INVENTION

The present invention discloses compositions suitable for topical use comprising a combination of a free sphingoid base and a ceramide. The topical compositions of the invention can be cosmetic as well as dermatologic compositions.

It is shown by the present invention that topical compositions comprising a combination of a free sphingoid base and a ceramide have a positive and beneficial effect on skin conditions associated with an impaired lipid barrier function. The synergistic effects of the combination of a free sphingoid base and a ceramide become even more apparent when the compositions according to the invention are used for the treatment of skin conditions wherein an impaired lipid barrier function further is associated with a deranged regulation of cell growth and differentiation, an inflammatory condition and/or an infectious state. Said deranged regulation of cell growth and differentiation is characterized by conditions like hyperproliferation of keratinocytes, decreased differentiation of keratinocytes and/or decreased desquamation of corneocytes.

The present invention shows that the presence of a free sphingoid base especially improves the efficacy of the composition of the invention with regard to its antiinflammatory and/or its antimicrobial activity. It is shown that this efficacy improvement is due to, in particular, an antimicrobial and antiinflammatory activity of the free sphingoid base.

The free sphingoid base present in the composition according to the invention has a general structure according to Formula 1:

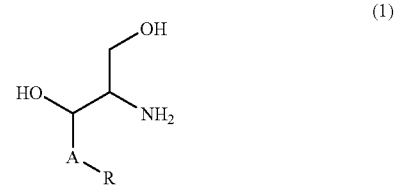

(1)

wherein:

A is $CH_2$—$CH_2$, $CH$=$CH$ or $C(H)OH$—$CH_2$, and

R is a straight chain or branched alkyl group having 10 to 22 carbon atoms which may optionally contain one or more double bonds and/or may optionally be substituted with one or more hydroxyl groups, preferably is a straight chain alkyl group having 12 to 18 carbon atoms, more preferably is a straight chain alkyl group having 13 carbon atoms.

The ceramide present in the composition according to the invention has a general structure according to Formula 2:

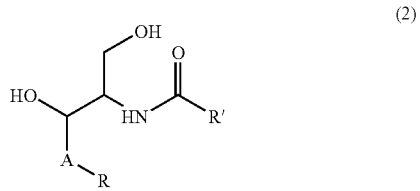

(2)

wherein:

A and R are defined as above, and

R' is a straight chain or branched alkyl group having 13 to 55 carbon atoms, preferably 15 to 50 carbon atoms, more preferably 17 to 44 carbon atoms; the alkyl chain may optionally be interrupted by an oxygen atom or by an internal ester group; may optionally contain one or more double bonds; and may optionally be substituted with one or more hydroxyl groups.

The free sphingoid base which is present in the composition of the invention preferably is a sphingosine, a sphinganine or a phytosphingosine. More preferably, the free sphingoid base is a phytosphingosine obtainable by deacetylation of tetraacetylphytosphingosine obtainable by fermentation of the yeast *Pichia ciferri*.

The ceramide which is present in the composition of the invention can be extracted from a natural source, for instance a mammalian source, or can be obtained via synthetic means. An example of a suitable chemical synthesis method is the acylation of a free sphingoid base with a suitable fatty acid, for instance via the acylation method as disclosed in international patent application WO93/20038.

In a preferred embodiment of the invention, the ceramide present in the composition of the invention is a ceramide which corresponds in stereochemical configuration to a ceramide isolatable from mammalian skin. Ceramides as isolated from mammalian skin typically can be subdivided in six heterogeneous classes of compounds, ceramide 1, 2, 3, 4, 5, 6I and 6II. In general, these ceramides consist of a free sphingoid base in amide linkage with a nonhydroxy or an α-hydroxy fatty acid, or an ω-hydroxy fatty acid esterified with an additional fatty acid. A ceramide which corresponds in stereochemical configuration to a mammalian skin ceramide may for instance be obtained by acylation of *Pichia ciferri*-derived phytosphingosine. Examples of such ceramides are the ceramides disclosed in international patent applications WO93/20038, WO95/11881, WO95/25716 and WO96/10557.

Within the context of the present invention, an individual ceramide as well as a mixture of two or more different ceramides can be applied in a topical composition.

In that regard, said mixture of two or more different ceramides may include various ceramide combinations, the choice of a specific combination depending among others on the desired application.

A combination of two or more representatives of each ceramide class may for instance be applied, since said combination may lead to an increased ceramide solubility in the composition according to the invention. Individual ceramides may tend to crystallize and consequently become inert and unfunctional.

A further option is a combination of, on the one hand, a sphinganine- and/or sphingosine-containing ceramide and, on the other hand, a phytosphingosine-containing ceramide (e.g. ceramide 1 and/or 2 and/or 4/5 with ceramide 3 and/or Ceramide 6). Such a combination consists of two types of ceramides having a head group which differs in hydrophilicity and this may increase barrier enhancing properties of the same. For the same reason, a combination is feasible of a ceramide containing an α-hydroxy fatty acid with a ceramide containing a non-hydroxylated fatty acid (e.g. ceramide 1 and/or ceramide 2 and/or ceramide 3 with ceramide 4/5 and/or ceramide 6).

Further feasible is a combination of a ceramide containing a medium chain fatty acyl group of 16 to 22 carbon atoms with a ceramide containing a long chain fatty acyl groups of 22 to 32 carbon atoms, since such a combination naturally occurs in the stratum corneum and may also be important for a stronger barrier structure (Bouwstra et al. (1996), J. Lipid Res. 37, 999-1011).

The composition of the invention optionally may comprise one or more additional skin lipid compounds, such as cholesterol, cholesterol esters like cholesteryl sulphate, free fatty acids like palmitic, stearic, behenic, oleic and/or linoleic acid and/or other sphingolipids like glycoceramides. The composition of the invention may further comprise ceramide compounds having a short-chain acyl group, said short chain acyl group optionally being a-hydroxylated (so-called short-chain ceramides).

With respect to glycoceramides, two groups of these compounds are typically distinguished, i.e. cerebrosides and gangliosides. A cerebroside is understood to be a glycoceramide wherein a monosaccharide, mostly glucose or galactose, is attached to the oxygen of the —$CH_2OH$ group of the ceramide according to Formula 2. In gangliosides oligosaccharides, frequently including sialic acid, are attached to the same.

With respect to short-chain ceramides, a short chain acyl group is meant to comprise acyl groups having 2 to 14 carbon atoms. A preferred ceramide with a short-chain acyl group is acetylphytosphingosine. Examples of ceramides having a short-chain α-hydroxyacyl group are disclosed in international patent application WO95/29151.

In one embodiment of the invention, a composition comprising a free sphingoid base and a ceramide may contain as the sole type of ceramide compound a glycoceramide or a short-chain ceramide. In another embodiment, the ceramide compound in the composition of the invention may be a mixture of a glycoceramide and a short-chain ceramide.

Next to the free sphingoid base and the ceramide, other active ingredients may be present in the composition according to the invention. For instance, the combination of a free sphingoid base and a ceramide may advantageously be applied in combination with a conventional antiinflammatory and/or antimicrobial agent, where said conventional antiinflammatory and/or antimicrobial agent may be applied in substantially lower concentrations than typically used, because of the activity of the free sphingoid base.

An example of a conventionally used antiinflammatory agent is a corticosteroid.

Other active ingredients which may advantageously be applied in the compositions according to the invention, in combination with a free sphingoid base and a ceramide, are agents which have an effect on skin appearance.

For instance, yeast β-glucan may be applied in the composition according to the invention to reduce UV-induced erythema. Skin-peeling agents, like α-hydroxyacids, urea, salicylic acid or proteases, may be applied in the composition according to the invention to improve desquamation and/or decrease roughness of the skin. Retinoids may be applied in the composition according to the invention to stimulate the mitotic and metabolic activity of epidermal cells. Vitamin C and/or E may be applied in the composition of the invention for their antioxidant activity on skin components, which favours their application as, for instance, antiageing agents.

The free sphingoid base as well as the ceramide may be present in the composition according to the invention in a concentration of 0.001 to 10%, preferably in a concentration of 0.005 to 5%, more preferably in a concentration of 0.01-2%, most preferably in a concentration of 0.02-1.0%.

The ratio of free sphingoid base to ceramide in the composition according to the invention may lie within a range of 1 to 10 to 10 to 1. Preferably, said ratio may vary from about 1 to 5 to about 5 to 1. More preferably, said ratio may vary from about 1 to 5 to about 1 to 1.

Next to the active ingredients, the topical preparations of the invention further include the usual components.

The composition comprises a vehicle to enable the active ingredients to be conveyed to the skin.

The vehicle enables proper application on skin and/or hair, to provide both a dermatological as well as a cosmetic treatment. The composition may comprise a solid, semi-solid or liquid cosmetically and/or physiologically acceptable vehicle. The nature of the vehicle will depend upon the method chosen for topical administration of the composition. Vehicles other than water can include liquid or solid emollients, solvents, humectants, thickeners, powders, surfactants, which are also sometimes designated as emulsifiers, solubilizers, propellants and other active ingredients.

Emollients can be classified under such general chemical categories as (fatty acid) esters, fatty acids, (fatty) alcohols, polyols, (natural) waxes, natural oils, silicone oils, both volatile and non-volatile and hydrocarbons such as mineral oil, petroleum jelly, vaseline, squalens and (iso)paraffin.

Surfactants including emulsifiers may be cationic, nonionic, anionic or amphoteric in nature. A single type of surfactant and/or combinations of surfactants may be employed.

Illustrative for nonionic surfactants are alkoxylated compounds based upon fatty alcohols, fatty acids and sorbitan.

Anionic-type surfactants may include fatty acid soaps, lauryl sulphate salts, lauryl ether sulphate salts, alkyl benzene sulphonates, alkyl acid phosphates. Amphoteric surfactants include materials as dialkylamine oxide and various types of betaines, such as cocoamido propyl betaine.

Cationic surfactants comprise quaternary ammonium compounds (Quats) such as cetyl trimethyl ammonium chloride or bromide.

A special class of surfactants are silicone surfactants, which are high molecular weight polymers of dimethyl polysiloxane with polyoxyethylene and/or polyoxypropylene side chains having a molecular weight of 10.000 to 50.000 D.

In general, surfactants used for the preparation of emulsions include emulsifiers comprising compounds having a HLB (hydrophilic/lipophilic balance) value which is in the lower as well as in the higher ranges, i.e. compounds which are able to form a water-in-oil as well as compounds which are able to form an oil-in-water emulsion, respectively. Typically, if a water-in-oil emulsion is required, the HLB value of the emulsifier or mixture of emulsifiers varies between about 1 and 7. For an oil-in-water emulsion, said HLB value is higher than about 7.

Specific emulsifiers comprise emulsifiers which are able to form a lamellar phase (liquid crystalline or gel phase). Lamellar phases are formed at the oil-water interphase of an oil-in-water emulsion and directly incorporate the free sphingoid base and the ceramide. Examples of such specific emulsifiers are:

1. Fatty acids+neutralized fatty acids:
   e.g. stearic acid, isostearic acid, etc.
2. Glyceryl mono-fatty acid ester+neutralized fatty acids:
   glyceryl stearate SE, glyceryl oleate SE
3. Glyceryl mono-fatty acid ester+ethoxylated fatty alcohols/esters:
   glyceryl stearate+Ceteareth-20+various
   glyceryl stearate+PEG-20 glyceryl stearate
4. High-ethoxylated fatty alcohols+low-ethoxylated fatty alcohols (+polar emollients):
   Steareth-2+Steareth-21 (+PPG-15 stearyl ether/fatty alcohol)
   Ceteareth-6+Ceteareth-25
   Cetearyl Alcohol+Ceteareth-20
5. Various polyglyceryl esters+combinations:
   polyglyceryl-3-methyl glucose distearate.
   polyglyceryl-10 pentastearate+behenyl alcohol+sodium stearoyl lactylate
   polyglyceryl-2 isostearate (or resp. di/tri/tetra isostearate)
   polyglyceryl-3 diisostearate
6. Various other sugar-esters:
   Cetearylglucoside+Cetearyl alcohol
   methyl glucose sesquistearate+PEG-20 methyl glucose sesquistearate
   Sorbitan stearate+sucrose cocoate
   Sorbitan stearate+polysorbate 60
   sucrose esters (laurate/palmitate/stearate/oleate/isostearate)
7. Lecithins and other Phospholipids:
   lecithin Propellants include propane, butane, isobutane, dimethyl ether, chlorofluoroalkanes, carbon dioxide, nitrous oxide.

Solvents include ethyl alcohol, methylene chloride, isopropanol, ethyl ethers such as ethoxyethanol and butoxyethanol, acetone, tetrahydrofuran, dimethyl formamide, DMSO, propylene glycol, butylene glycol.

Humectants include proteins and protein hydrolysates, amino acids, sorbitol, glycerin, sorbitol, glycols preferably PEG 200-4000 and other polyols.

Thickeners include cross linked polyacrylates, silicone gums and polysaccharide gums such as xanthan, carrageenan, gelatin, pection and locust beans gum, hyaluronic acid and carboxylic group-containing polymers Powders include chalk, talc, starch, kaolin, clays, silicates, carboxyvinyl polymers.

Other active ingredients include:
anti-oxidants like butyl hydroxy toluene, ascorbic acid and salts, EDTA, hydroquinone, tocopherols, gallates;
preservatives like para-hydroxy benzoate esters, sorbic acid, EDTA, quaterniums, benzoic acid, imidazolidinyl urea, (benzyl)alcohol;
enzyme regulators like vitamins and other co-factors;
penetration enhancers like mono- or di-esters of C2 to C10 alcohols and C8 to C18 fatty acids, propanols, urea, sugar esters, POE esters or ethers of fatty acids and/or alcohols, butan-1,4 diol, tetrahydrofuran, salicylate salts, pyrrolidones, N-alkyl-aza-cycloheptanones, oleic acid, linoleic acid;

sunscreens, blocking UV light, like PABA's, cinnamate and salicylate derivatives;

other actives like coloring agents or perfumes.

The combination of the said components can account for 5 to 99% of the composition.

The positive and beneficial effects of the compositions according to the invention on affected skin areas are various and are summarized as follows: a reduction of redness, dryness, roughness and/or scaling of the skin, a reduction of pruritis, a reduction of skin lesions, an improvement in healing of small wounds, a decrease of inflammatory symptoms in affected areas, a decrease of an infectious state of the skin in affected areas.

Examples of skin conditions which benefit from topical application of a composition according to the invention are psoriasis, atopic dermatitis, irritant and allergic contact dermatitis, seborrheic and sebostatic dermatitis, photodermatitis (UV-induced erythema), acne, ichthyosis, xerosis, aged skin. The skin infections which benefit from topical application of the compositions of the invention include bacterial, fungal, yeast and viral infections. For example dandruff, impetigo, Pityriasis vesicolor, Tinea corporis, Rosacea, Herpes, venereal diseases.

For specific skin conditions, i.e. wounds, burns, scalds, a combination of a free sphingoid base and a cerebroside is preferred, since cerebrosides (contrary to ceramides) tend to stimulate the proliferation of keratinocytes.

On the other hand, for skin diseases where, next to an impaired barrier function and skin infections, hyperproliferation, reduced differentation and reduced desquamation are general symptoms, the inclusion of ceramides with a short-chain acyl group may be advantageous. These short-chain ceramides will have the additional effect that they are cell-permeable and known to reduce proliferation, increase differentiation and increase desquamation.

The present invention is exemplified by several formulations and by an efficacy study using test persons with different skin disorders. Furthermore, the antiimflammatory activity of a free sphingoid base is demonstrated.

EXAMPLE 1

Formulations Comprising Phytosphingosine and Several Ceramides

Below, several examples of suitable formulations according to the invention are given.

The ceramides and the free sphingoid base used in these formulations are the following:

Ceramide III: N-stearoyl-phytosphingosine
Ceramide IIIB: N-oleoyl-phytosphingosine
Ceramide VI: N-alpha-hydroxystearoyl-phytosphingQsine
Phytosphingosine: 2-amino-octadecane-1,3,4-triol
Phytoceramide I: N-stearoyloxyheptacosanoyl-phytosphingosine Waterless Barrier Cream I
comprising Ceramide III, Ceramide VI and Phytosphingosine

| INCI-name | Trade name | Percentage (% w/w) |
|---|---|---|
| Hydrogenated lecithin | | 4.0 |
| Glycerin | | 48.0 |
| Butylene glycol | | 18.0 |
| Jojoba oil | | 5.0 |

-continued

| INCI-name | Trade name | Percentage (% w/w) |
|---|---|---|
| Propylene glycol dicaprylate/dicaprate | Miglyol 840 (Huls) | 10.0 |
| Isocetyl alcohol | Eutanol G16 (Henkel) | 3.0 |
| Tocopheryl acetate | | 5.0 |
| Dimethicone copolyol eicosonate | | 5.0 |
| Ceramide 3 | Ceramide III (Cosmoferm) | 0.5 |
| | Ceramide IIIB (Cosmoferm) | 0.5 |
| Ceramide 6 | Ceramide VI (Cosmoferm) | 0.5 |
| Phytosphingosine | Phytosphingosine (Cosmoferm) | 0.5 |

Waterless Barrier Creams II and III comprising Ceramide III, Ceramide VI and Phytosphingosine, and additionally cholesterol and stearic acid

| INCI-name | Trade name | Percentage (% w/w) | |
|---|---|---|---|
| Hydrogenated Lecithin | Amisol 905 (Lucas Meyer) | 4.0 | 4.0 |
| Glycerin | | 30.0 | 24.0 |
| Butylene glycol | | 20.0 | 20.0 |
| Glycero phosphoilipids | Biophilic S (Lucas Meyer) | 1.5 | 1.5 |
| Jojoba oil | | 5.0 | 5.0 |
| Paraffin | | 10.0 | 10.0 |
| Propylene glycol dicaprylate/ dicaprate | Myritol PC (Henkel) | 10.0 | 10.0 |
| Isocetyl alcohol | Eutanol G16 (Henkel) | 8.0 | 8.0 |
| Hydrogenated vegetable oil | Cremeol HF52 (Aarhus) | 5.0 | 5.0 |
| Tocopheryl acetate | BASF | 5.0 | 5.0 |
| Ceramide 3 | Ceramide III (Cosmoferm) | 0.25 | 1.25 |
| | Ceramide IIIB (Cosmoferm) | 0.25 | 1.25 |
| Ceramide 6 | Ceramide VI (Cosmoferm) | 0.25 | 1.25 |
| Phytosphingosine | Phytosphingosine (Cosmoferm) | 0.25 | 1.25 |
| Cholesterol | | 0.25 | 1.25 |
| Stearic acid | Unichema | 0.25 | 1.25 |

Amisol 905 40% Hydrogenated lecithin, 30% Glycerin, 30% Butylene glycol.

Percentages have been corrected for glycerin and butylene glycol in the INCI-formulation Barrier Cream IV comprising Phytoceramide I, Ceramide III and IIIB, Ceramide VI, Phytosphingosine and Acetyl-phytosphingosine

| INCI-name | Trade name | Percentage (% w/w) |
|---|---|---|
| Lecithin (and) C12-16 alcohols (and) palmitic acid | Biophilic S (Lucas Meyers) | 2.0 |
| Polyglyceryl-3 Methylglucose Distearate | Tego Care 450 (Goldschmidt) | 2.0 |

-continued

| INCI-name | Trade name | Percentage (% w/w) |
|---|---|---|
| Cetearyl alcohol | Lanette O (Henkel) | 1.0 |
| Propylene glycol dicaprylate/dicaprate | Myritol PC (Henkel) | 10.0 |
| Isocetyl alcohol | Eutanol G16 (Henkel) | 10.0 |
| Rice Bran oil | | 5.0 |
| Tocopheryl acetate | BASF | 2.0 |
| Ceramide 3 | Ceramide III (Cosmoferm) | 0.5 |
| | Ceramide IIIB (Cosmoferm) | 0.5 |
| Ceramide 6 | Ceramide VI (Cosmoferm) | 0.5 |
| Phytosphingosine | Phytosphingosine (Cosmoferm) | 0.5 |
| Ceramide 1 | Phytoceramide 1 (Cosmoferm) | 0.1 |
| Acetyl-Phytosphingosine | C2-Ceramide (Cosmoferin) | 0.1 |
| Stearic acid | | 0.5 |
| Cholesterol | | 0.5 |
| Butylene glycol | | 6.0 |
| Mixed parabens in Phenoxyethanol | Phenonip | 0.6 |
| Water | | 64.4 |

Liposomal Formulation comprising Ceramide III, Ceramide IIIB, Ceramide VI and phytosphingosine, and additionally cholesterol and linoleic acid

| INCI-name | Trade name | Percentage (% w/w) |
|---|---|---|
| Sodium lauroyl lactylate | | 9.0 |
| Tocopherol acetate | | 0.01 |
| Carbomer | | 0.3 |
| Ceramide 3 | Ceramide III (Cosmoferm) | 0.2 |
| | Ceramide IIIB (Cosmoferm) | 0.2 |
| Ceramide 6 | Ceramide VI (Cosmoferm) | 0.1 |
| Phytosphingosine | Phytosphingosine (Cosmoferm) | 0.5 |
| Linoleic acid | | 0.25 |
| Cholesterol | | 0.25 |
| Water | | 89.2 |

EXAMPLE 2

Efficacy Evaluation of Barrier Cream I

To test the efficacy of a composition comprising a free sphingoid base and a ceramide, barrier cream I was applied daily by several test persons suffering from various skin disorders. The results are indicated in Table 1. It is clear that the use of a barrier cream according to the invention results in a significant improvement of the affected skin areas.

TABLE 1

| Person | Condition | Application | Effect |
|---|---|---|---|
| 1 | Psoriatic lesions on right leg | 8 weeks 1* per day | Strong improvement; lesions have practically disappeared; small wounds appear to heal faster |
| 2 | Dry xerotic skin, in particular on cheeks | 3 weeks 1* per day | Clear improvement; skin is less scaly and red |
| 3 | Ichtyosis over whole body | 8 weeks 1* per day, only on the face | Improvement is visible; no itching feeling like with urea cream |
| 4 | Atopic skin | 4 weeks 1* per day | Improvement; comparable to corticosteroid cream |
| 5 | Psoriatic lesions on the elbow | 4 weeks 1* per day | Improvement; lesions return upon withdrawal |

EXAMPLE 3

Effect of the Free Sphingoid Base Phytosphingosine on the Secretion of Cytokines as a Marker for Antiinflammatory Activity Principle:

The effect of phytosphingosine was assessed ex vivo on excised human skin explants.

The explant was exposed to UV-B rays as a physical, proinflammatory stress.

The antiinflammatory effect of phytosphingosine was evaluated by measurement of the amount of the cytokine IL-1α secreted in the incubation medium of the skin explants.

Protocol:

Preparation of the human skin explants obtained after plastic surgery using standard techniques.

Application of the test product:

resp. 0% (Placebo), 0.2 and 0.5% phytosphingosine (PS) in Propylene glycol:Ethanol (60:40).

Dexamethasone (1 μM) was used as the reference product.

The products were applied before and after irradiation (~2 mg/cm$^2$)

IL-1α secretion was measured in the incubation medium of the skin explants, using a standard ELISA technique.

Each experimental condition was performed in triplicate.

Results:

| Before UV-B | After UV-B | Dexamethasone | Placebo | 0.2% PS | 0.5% PS |
|---|---|---|---|---|---|
| 48 | 205 | 116* | 165 | 82* | 92* |

*Significant effect $p < 0.05$
- Results are expressed in pg per ml IL-1α

The invention claimed is:

1. A composition for topical use comprising a combination of a free sphingoid base and a ceramide, said free sphingoid base having a general structure according to Formula 1:

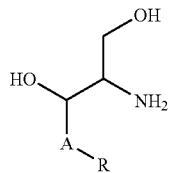

(1)

wherein:
  A is C(H)OH-CH$_2$, and
  R is a straight chain or branched alkyl group having 10 to 22 carbon atoms, and said ceramide having a general structure according to Formula 2:

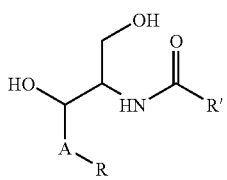

(2)

wherein:
  A and R are defined as above, and
  R' is a straight chain or branched alkyl group having 13 to 55 carbon atoms; may
    optionally contain one or more double bonds; and may optionally be substituted with one or more hydroxyl groups.

2. The composition of claim 1, wherein the free sphingoid base is phytosphingosine.

3. The composition of claim 1, wherein the ceramide is a mixture of two or more different ceramides.

4. The composition of claim 1, wherein the composition further comprises one or more additional skin lipid compounds.

5. The composition of claim 1, wherein a ceramide is present in addition to the ceramide according to Formula 2 which is selected from the group of glycoceramides and short chains ceramides.

6. The composition of claim 1 which is a dermatological composition.

7. The composition of claim 1 which is a cosmetic composition.

8. A method of making a topical composition for the treatment of a skin condition associated with an impaired barrier function which comprises adding the composition of claim 1 with a topically suitable carrier.

9. The method of claim 8, wherein said skin condition is further associated with a condition selected from the group consisting of a deranged regulation of cell growth and differentiation, an antiinflammatory condition or an infectious state.

10. A method for the treatment of a skin condition associated with an impaired barrier function comprising the topical application of a composition according to claim 1.

11. The method of claim 10, wherein said skin condition is further associated with a condition selected from the group consisting of a deranged regulation of cell growth and differentiation, an antiinflammatory condition or an infectious state.

12. The method of claim 11 which is a non-therapeutical method.

13. The composition of claim 1, wherein
  R is a straight chain or branched alkyl group having 12 to 18 carbon atoms; and
  R' is a straight chain or branched alkyl group having 15 to 50 carbon atoms which may optionally contain one or more double bonds; and may optionally be substituted with one or more hydroxyl groups.

14. The composition of claim 13, wherein
  R is a straight chain or branched alkyl group having 13 carbon atoms; and
  R' is a straight chain or branched alkyl group having 18 carbon atoms which may optionally contain one or more double bonds; and may optionally be substituted with one or more hydroxyl groups.

15. The composition of claim 14, wherein the free sphingoid base is phytosphingosine and the ceramide is selected from the group consisting of N-stearoyl-phytosphingosine, N-oleoyl-phytosphingosine, N-alpha-hydroxystearoyl-phytosphingosine and mixtures thereof.

* * * * *

UNITED STATES PATENT AND TRADEMARK OFFICE
CERTIFICATE OF CORRECTION

PATENT NO.       : 7,597,899 B2                                             Page 1 of 1
APPLICATION NO.  : 10/463277
DATED            : October 6, 2009
INVENTOR(S)      : Johannes Wilhelmus Jacobus Lambers It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 726 days.

Signed and Sealed this

Twenty-eighth Day of September, 2010

David J. Kappos
*Director of the United States Patent and Trademark Office*